US005704097A

United States Patent [19]

Rahav

[11] Patent Number: 5,704,097

[45] Date of Patent: Jan. 6, 1998

[54] REUSABLE SECURITY SEAL

[76] Inventor: Avraham Rahav, P.O.B. 33848, Haifa 31338, Israel

[21] Appl. No.: 422,562

[22] Filed: Apr. 14, 1995

[51] Int. Cl.$^6$ .......... A61B 5/117

[52] U.S. Cl. .......... 24/16 PB; 24/17 AP; 40/633; 40/665; 292/317

[58] Field of Search .......... 24/16 PB, 30.5 P, 24/30.5 R, 16 R, 17 A, 17 AP; 292/317, 320, 321, 325; 40/633, 665, 306, 309, 310

[56] References Cited

U.S. PATENT DOCUMENTS

| | | | |
|---|---|---|---|
| 515,747 | 3/1894 | Carr | 24/16 PB |
| 1,679,963 | 8/1928 | Eason | 292/320 |
| 2,893,143 | 7/1959 | Mosher, Jr. et al. | 40/633 |
| 3,146,012 | 8/1964 | King, Sr. | 292/320 |
| 3,362,412 | 1/1968 | Moller | 24/16 PB |
| 3,556,575 | 1/1971 | Farkas . | |
| 4,299,417 | 11/1981 | McClure | 292/320 |
| 4,630,384 | 12/1986 | Breen | 40/665 |

FOREIGN PATENT DOCUMENTS

| | | | |
|---|---|---|---|
| 349670 | 10/1990 | European Pat. Off. | 40/310 |
| 30978 | 12/1897 | United Kingdom | 40/310 |
| 5486 | 2/1913 | United Kingdom | 40/665 |
| 1594207 | 7/1981 | United Kingdom | 292/320 |

*Primary Examiner*—Peter M. Cuomo
*Assistant Examiner*—Hanh V. Tran
*Attorney, Agent, or Firm*—Gottlieb, Rackman & Reisman, P.C.

[57] ABSTRACT

A reusable security seal comprising a first member including a plurality of frangible sections, each frangible section having a first clasp portion and an identity associated therewith is provided. A housing is coupled to a first end of the first member and includes a second clasp portion disposed at least partially therein for cooperating with the first clasp portion. The first member and the housing form a closed loop extending between the cooperating clasp portions. The first clasp portion and the second clasp portion are adapted for substantially locking engagement, so that pressure applied to the closed loop will cause at least one of the frangible sections to break before the clasp portions will unlock.

22 Claims, 2 Drawing Sheets

REUSABLE SECURITY SEAL

BACKGROUND OF THE INVENTION

This invention relates generally to a security seal of the kind used for securing transport containers, warehouse doors, army depots, valves, taps in mobile petroleum carriers and the like, so as to protect against unauthorized tampering, and in particular, to a security seal of this type which is reusable.

Security seals are generally supplied for single use, so that removing the seal can only be accomplished by breaking the seal in such a manner that it is no longer usable. Security seals are commonly mounted through respective apertures projecting from adjacent doors in a transport container and are mounted after loading the transport container and prior to transit thereof, so that when the transport container reaches its destination inspection of the security seal may serve to ensure that the doors of the container have not been tampered with during transit.

After removal of the security seal from the doors of the transport container, the container is unloaded and very often is then sent on to a further destination with a new load, thereby requiring the fixation of another security seal. Although security seals are relatively inexpensive, it will be appreciated that haulage contractors must purchase security seals in mass quantities and that the ability to reuse a security seal several times would result in very significant savings to the haulage contractor. However, to date the design of conventional security seals has militated against their reuse. On the one hand, the security seal must be somehow broken in order to permit access to the load and, on the other hand, such breakage is itself indicative of unauthorized tampering with the security seal if this is done during transit.

It is therefore desirable to provide a reusable security seal that is inexpensive to manufacture, simple to use and decreases costs to the end-user.

SUMMARY OF THE INVENTION

Generally speaking, in accordance with the invention, a reusable security seal includes a first member including a plurality of frangible sections each frangible section having a first clasp portion and an identity associated therewith. A housing is coupled to a first end of the first member and includes a second clasp portion disposed at least partially therein for cooperating with the first clasp portion. The first member and the housing form a closed loop extending between the cooperating clasp portion. And the first clasp portion and the second clasp portion are adapted to lock, so that pressure applied to the closed loop will cause at least one of the frangible sections to break before the clasp portion will unlock.

Preferably, the first member is divided into a plurality of frangible sections, each having a respective identity code embossed thereon (i.e. an identification number) and having an aperture formed therein which engages a resiliently mounted claw within the housing. In the preferred embodiment, the housing is substantially closed and includes a pair of slots at opposite ends thereof. One slot receives the frangible section of the first member inserted therein. The frangible member cannot be removed from this slot. The second slot is for the frangible member to be removed from.

The frangible member is insertable within the first slot and removable from the second slot of the housing because the claw of the housing engages the aperture of the frangible section to lock the frangible section in place. When the frangible section is separated from the remainder of the first member it can be removed from the housing through the second slot, because the aperture in the frangible section can ride over the resiliently mounted claw in the direction of the second slot. Alternatively, pulling on the closed loop (pulling the frangible section toward the first slot), causes the claw to engage an inside edge of the aperture thereby preventing withdrawal of the flexible strip from the housing. This in essence locks the frangible member in the housing.

In the preferred manner of use, the frangible section, locked within the housing is the section that is broken (i.e., separated from the first member). The frangible section remaining inside the housing is removed from the housing by pulling on a free end of the frangible section which protrudes from the housing. The frangible section must be pulled along the same direction as it was inserted into the housing to be removed (it can not be removed from the same slot it was inserted into).

Accordingly, it is an object of the invention to provide an improved reusable security seal.

It is another object of the invention to provide a reusable security seal that includes a plurality of frangible sections each having an identity associated therewith, and that identity is optionally hidden until the seal is broken and the identity is checked.

Still another object of the invention is to provide a reusable security seal that is low cost to manufacture.

Yet another object of the invention is to provide a reusable security seal that reduces waste of raw materials and is more healthy for the environment then previous security seals.

Still a further object of the invention is to provide a reusable seal that is usable at least thirty times.

Still other objects and advantages of the invention will in part be obvious and will in part be apparent from the specification and drawings.

The invention accordingly comprises a product possessing the features, properties, and the relation of components which will be exemplified in the product hereinafter described, and the scope of the invention will be indicated in the claims.

BRIEF DESCRIPTION OF THE DRAWINGS

For a fuller understanding of the invention, reference is had to the following description taken in connection with the accompanying drawings, in which.

DETAILED DESCRIPTION OF THE PREFERRED EMBODIMENT

Figures 1, 2, 3:
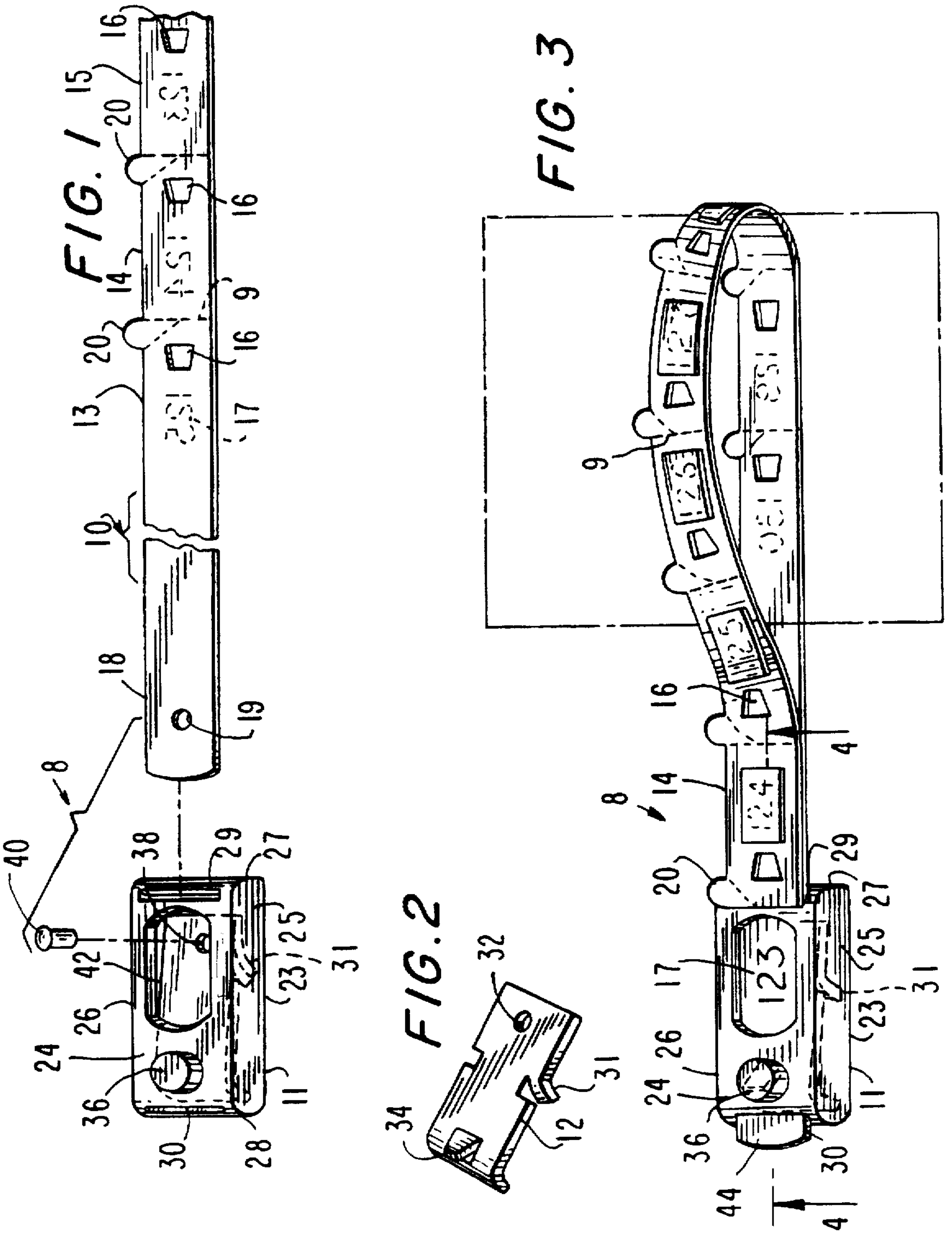
FIG. 1 is an exploded perspective view of a reusable security seal in accordance with a first embodiment of the invention with select interior elements shown in phantom.
FIG. 2 is a perspective view of the preferred embodiment of the clasp element which is normally located within the housing of a reusable security seal.
FIG. 3 is a perspective view of a reusable security seal shown with the first (band) member fed through the first slot of the housing.
Figure 4:
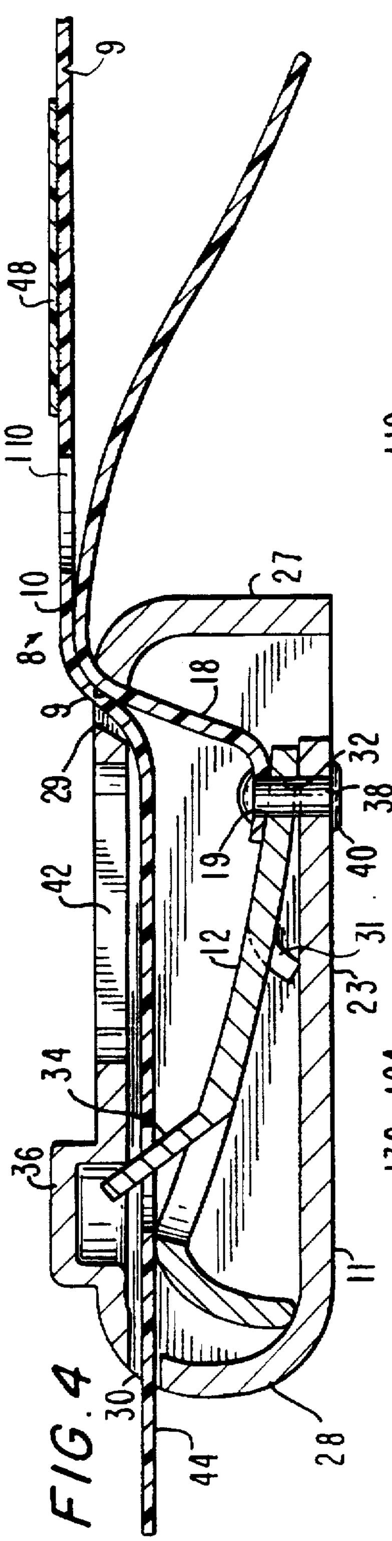
FIG. 4 is a partial cross-section view taken along line 4—4 of FIG. 3.

FIGS. 1 through 4 show a security seal according to a first embodiment of the invention, generally indicated at 8, which includes a flexible strip 10, a housing 11 and a clasp portion 12. Flexible strip 10 includes a plurality of frangible sections 13, 14 and 15 each having a respective aperture 16 therein, and a respective identify associated therewith comprising a serial number or identity code 17, embossed on a surface of flexible strip 10. (In the preferred embodiment, each seal will include at least thirty frangible sections.) Identity code 17 provides an identity for each frangible section 13, 14 and 15. Preferably, identity code 17 includes at least 3 digits. The identity code 17 can also include an alphabetic code which further expands the number of unique codes. The frangible sections are defined by grooves 9 formed in flexible strip 10 (the grooves are shown as dashed lines in the perspective views).

A first end 18 of the flexible strip 10 is provided with an aperture 19 and each of the frangible sections 13, 14 and 15 has associated therewith a corresponding lateral protrusion 20. Lateral protrusion 20 constitutes an arrest means which is itself frangible from flexible strip 10 attached to the respective section. As discussed in more detail below, when the flexible strip 10 is inserted into housing 11 the respective lateral protrusion 20 associated with the frangible section proximate to the frangible section disposed within housing 11, engages housing 11 and prevents further insertion of flexible strip 10 into housing 11.

Housing 11 comprises an essential fully enclosed rectangular box shaped member, and includes a lower surface 23 and an upper surface 24, a pair of sidewalls 25 and 26 and a pair of end walls 27 and 28. End walls 27 and 28 define a pair of slots 29 and 30 disposed in the respective end walls 27 and 28 in facing relation. The clasp portion 12 is provided at a first end thereof with an aperture 32 and is provided with an upwardly directed claw 34 at an opposite end thereof. Clasp 12 also includes two downwardly directed legs 31 that are provided to bear against the lower surface 23 of housing 11. Legs 31 are provided below window 42 in upper surface 24 to prevent tampering with the seal by deflecting clasp 12 through window 42. When assembled, clasp 12 is mounted within housing 11, such that the end of clasp 12 which contains aperture 32 abuts lower surface 23 of housing 11, and the opposite end of clasp 12 which contains claw 34 abuts the upper surface 24 of the housing 11, and is accommodated within a generally bulbous protrusion 36 of housing 11. The first end 18 of flexible strip 10 is inserted into first slot 29 of housing 11 and a single expansion rivet 40 is disposed within aperture 19 of flexible strip 10, aperture 32 of clasp 12 and an aperture 38 of lower surface 23 of housing 11. Rivet 40 fixedly secures clasp 12 and flexible member 10 to housing 11.

Operation of security seal 8 is facilitated by providing a window 42 in the upper surface 24 of housing 11. Window 42 permits identify code 17 of the frangible sections to be displayed therethrough when the frangible section is inserted into housing 11.

First end 18 of flexible strip 10 eventuates from first slot 29 of housing 11 while a second end 44 of flexible strip 10 is inserted into first slot 29 of housing 11 and emerges from second slot 30 thereof. First slot 29 is designed to be thick enough to accommodate only two thicknesses of flexible strip 10, and second slot 30 is designed to accommodate only a single thickness of flexible strip 10. This configuration prevents tampering with the seal through slots 29 and 30 by unauthorized personnel. Furthermore, window 42 is configured to be small enough (preferably not larger than 4 mm) that the seal can not be tampered with through window 42. An additional seal, formed of plexiglass or the like can be optionally coupled to housing 11 proximate to window 42 to prevent tampering with the seal through the window opening.

Each frangible section shown in FIG. 1 preferably has associated therewith a three digit serial number (identity code 17), thus allowing one thousand possible permutations. In order to allow a larger number of unique identities to be associated with the security seals, each identity code 17 can be provided with two portions; one of which is embossed on flexible strip 10 and the other of which is associated with housing 11. Thus, in the specific example shown in the figure, the provision of two additional digits on housing 11 provides for a maximum of five digits thereby increasing the maximum number of permutations to 100,000. It is also possible to provide a multidigit serial number on housing 11, so that each housing 11 is distinct from all others. This would further expand the number of unique seals. An added measure of security can be achieved by numbering the frangible section in a random sequence rather than sequentially as depicted in the figures. In other words, the exact coding system used can be modified to suit any particular purpose.

In use, flexible strip 10 is passed through opposing handles of a container or other closed structure (not shown) and a free end 44 (constituting a second end) of flexible strip 10 is inserted into the first slot 29 of housing 11 so as to emerge from second slot 30 therein while positioning identity code 17 of the endmost frangible section 13 in alignment with window 42 of housing 11. When inserted in this manner, flexible strip 10 forms a closed loop depending from housing 11. Endmost frangible section 13 which is disposed within housing 11 depresses resilient clasp portion 12 until aperture 16 of endmost frangible section 13, engages claw 34 in clasp portion 12. Clasp portion 12 then springs upward slightly so that the claw 34 emerges through aperture 16 and is seated within bulbous protrusion 36, thereby preventing removal of flexible strip 10 from housing portion 11 by pulling on the closed loop formed by flexible strip 10. The engagement of aperture 16, constituting a first clasp portion, and claw 34, constituting a second clasp portion, form a locking clasp arrangement. The free end 44 of flexible strip 10 protrudes from second slot 30 of housing 11. Second end 44 of flexible strip 10 cannot be extracted through second slot 30 of housing 11 due to the abutment of lateral protrusion 20 against housing 11.

When it is desired to remove security seal 8 from sealing a container, the endmost frangible section 13 is preferably broken from the remainder of flexible strip 10. This leaves the endmost frangible section 13 within housing 11 while, at the same time, leaving lateral protrusion 20 still connected to the remainder of flexible strip 10. Since, in this condition, lateral protrusion 20 is no longer connected to endmost frangible section 13, the latter may be removed from housing 11 simply by pulling free end 44 of flexible strip 10, whereupon endmost frangible section 13 is extracted from housing 11 without damaging clasp 12 therein.

Lateral protrusion 20 associated with what was endmost frangible section 13 of flexible strip 10 and which remains connected to the remainder of flexible strip 10 is removed from flexible strip 10, so that second frangible section 14 bearing its respective identity code 17 now becomes the endmost frangible section, and the security seal may be reused, as required, until all the frangible sections thereof have been broken.

It is desirable to have the identity code 17 covered, so that it is not visible by the shipper, or transporter of the container being shipped. Accordingly, with particular reference to FIG. 4, it is seen that a laminate, or cover layer 48 is provided and disposed on top of flexible member 10 to cover identity codes 17. This is why each identity code 17 is shown in phantom in FIGS. 1 and 3, except for the identity code appearing within window 42, where the cover layer 48 is removed, so that only the identity code appearing in the window is visible. In an alternative embodiment, the cover layer 48 is not removed from the identity code until after the seal is broken and the frangible section is extracted through second slot 30 of housing 11.

Figure 5:
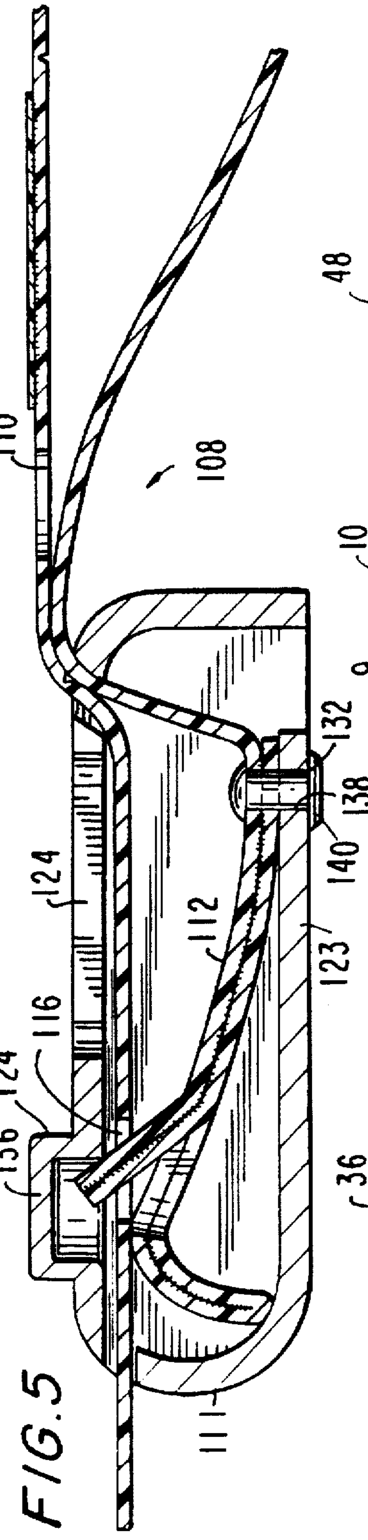
FIG. 5 is a partial cross-section view of a second embodiment of the invention.

Particular attention is next directed to the second embodiment of the invention disclosed in FIG. 5. FIG. 5 depicts a security seal, generally indicated at 108, which includes a flexible strip 110, a housing 111, and a clasp 112. The flexible strip includes a plurality of frangible sections (not shown, but the same as shown in FIGS. 1 and 2). Housing 111 is formed in the same configuration as disclosed above with regard to FIGS. 1–4, and flexible member 110 similarly includes substantially the same configuration as disclosed above.

The difference between security seal 8 and security seal 108 is in that flexible member 110 of FIG. 5 is formed integral with clasp 112. In FIG. 5, housing 111 comprises an essentially fully enclosed rectangular box-shaped member and includes a lower surface 123. A clasp portion 112 is provided at a first end with an aperture 132 which abuts against the lower surface 123 of housing 111. The opposite end of clasp 112 contains a claw 126 which abuts against an upper surface 124 of housing 111, and is accommodated within a generally bulbous protrusion 136 therein.

In the embodiment of FIG. 5, clasp portion 112 is integrally formed with flexible strip 110. In this embodiment, flexible strip 110 is semi-rigid, such that when doubled over in the region of clasp 112, claw 126 (which includes a double thick piece of flexible strip 110 coupled on itself) is rigid enough to lock flexible strip 110 within housing 111. Since clasp 112 is integrally formed with flexible strip 110, a single expansion rivet 140 is disposed through an aperture 132 in the double thick claw 112, and through an aperture 138 in bottom wall 123 of housing 111. The claw portion receives its rigidity and shape by being doubled over and coupled via normal processes, using, for example, adhesive, heat treatment or the like.

Figure 6:
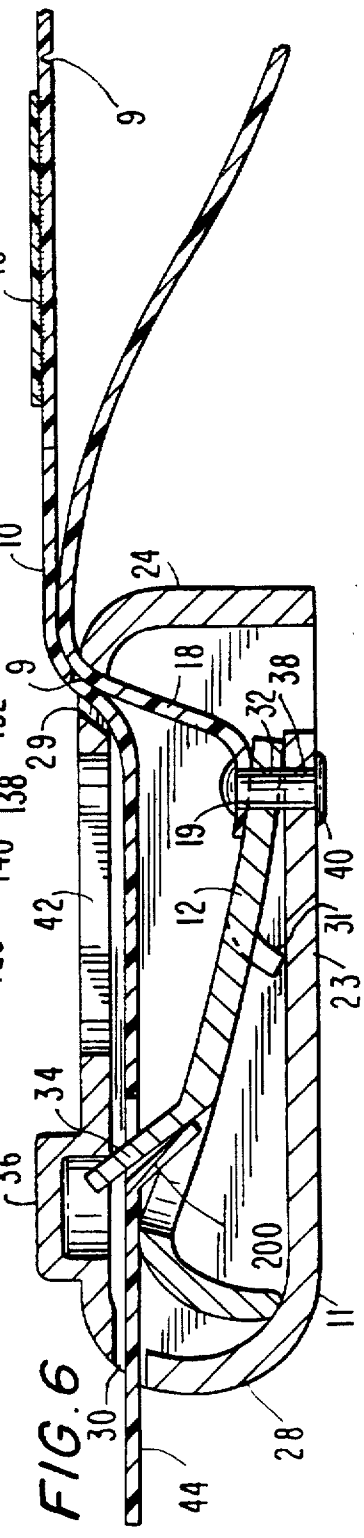
FIG. 6 is a partial cross-sectional view of a third embodiment of the invention.

The third embodiment, as disclosed in FIG. 6, is substantially the same as the first embodiment of 1–4; however, the only variation is that the apertures 16 formed in flexible strip 10 are not fully cut out. In other words, an additional locking feature is provided in the clasping technique. A flap 200 is provided proximate to aperture 16, and in locking engagement with claw 34 of clasp 12, thereby providing an additional locking feature.

Each embodiment includes an additional element that can be included in the other embodiments. For example, flap 200 can be incorporated within the embodiment of FIG. 5 to add greater strength to the clasp.

It will be appreciated that modifications may also be made to the security seal without departing from the spirit of the invention. For example, although the provision of the window 42 allows for easy manufacture of the security seal, as described, and also allows display of the identity code 17 therethrough, it may be preferred to emboss or otherwise mark the identity code on the protruding end of the flexible strip or, indeed, to identify each frangible section by means of a marking on an adjacent portion of the flexible strip. Furthermore, by eliminating window 42 the identity of the present frangible member can be kept a secret until the seal is broken.

While the flexible strip 10 is depicted as being formed of plastic, and housing 11 is depicted as being formed of metal, all components of the security seal may be formed of either metal or suitable plastic.

It is also clear that while the provision of lateral protrusion 20 is advantageous and prevents undesired waste of unused sections of the flexible strip, the lateral protrusion 20 is optional in the sense that the principle of the invention may be employed, even without the provision of lateral protrusion 20.

It will thus be seen that the objects set forth above, among those made apparent from the preceding description, are efficiently attained and, since certain changes may be made in the above article without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A reusable security seal, comprising:

a first member, including a plurality of frangible sections, each frangible section having an aperture and an individual unique identity marked thereon;

a housing coupled to a first end of the first member and including a clasp portion disposed at least partially therein for cooperating with one of the apertures;

said first member and the housing forming a closed loop extending between the cooperating clasp portion and aperture; and said aperture and said clasp portion being adapted for substantially locking engagement, so that pressure applied to the closed loop will cause at least one of said frangible sections to break before said locked aperture and clasp portion will unlock.

2. The reusable security seal as claimed in claim 1 wherein said housing includes a first slot and a second slot at opposite ends thereof for inserting therethrough a second end of said first member.

3. The reusable security seal as claimed in claim 2 wherein the second end of the first member is inserted into the first slot in order to form the closed loop.

4. The reusable security seal as claimed in claim 3 wherein one of said frangible sections that is locked within the housing may be removed through the second slot.

5. The reusable security seal as claimed in claim 3 further comprising a frangible arrest means associated with each of the frangible sections for engaging the housing proximate the first slot to prevent adjacent frangible sections from being inserted into the housing.

6. The reusable security seal as claimed in claim 2 wherein a window is provided on the housing between the first and second slots for displaying the identity of the frangible section located within the housing.

7. The reusable security seal as claimed in claim 2 wherein the clasp portion is a claw resiliently mounted in said housing.

8. The reusable security seal as claimed in claim 7 wherein said claw is resiliently mounted to said housing facing said second slot, so that said aperture may ride over the claw when the said first member is inserted into the housing and the second end of the said first member is withdrawn therefrom, and so that said claw engages an internal edge of the aperture when tension is applied to a portion of said closed loop proximate said first slot of said housing.

9. The reusable security seal as claimed in claim 8 wherein said clasp portion include a resilient plate mounted inside said housing.

10. The reusable security seal as claimed in claim 9 wherein said resilient plate is fixed to a lower inside surface of said housing towards said first slot and a bulbous dome is formed in an upper surface of said housing towards the second slot for accommodating said claw.

11. The reusable security seal as claimed in claim 9 wherein said resilient plate includes at least one leg for supporting said plate.

12. The reusable security seal as claimed in claim 1 wherein the first member and the clasp portion are co-anchored to the housing.

13. The reusable security seal as claimed in claim 12 wherein the first member and the clasp portion are riveted to the housing by a single rivet.

14. The reusable security seal as claimed in claim 1 wherein said first member and said clasp portion are integrally formed.

15. The reusable security seal as claimed in claim 1 wherein said housing is completely closed except for a first slot and second slot located at opposite ends of said housing and being sized to receive said first member therethrough.

16. The reusable security seal as claimed in claim 1, wherein said identity is located on the surface of said first member.

17. The reusable security seal as claimed in claim 16 further including cover means for hiding the identity of said frangible sections.

18. The reusable security seal as claimed in claim 17 wherein said cover means is selectively removable from each said frangible section.

19. A reusable security seal, comprising:

a first member including a plurality of frangible sections with each frangible section having an aperture and an identity associated therewith;

a housing coupled to a first end of the first member and including a clasp portion disposed at least partially therein for cooperating with one of said apertures, said first member and housing forming a closed loop extending between the cooperating aperture and clasp portion;

each of said apertures and said clasp portion being adapted for substantially locking engagement so that pressure applied to the closed loop will cause at least one of said frangible sections to break before said aperture and clasp portion will unlock;

wherein said housing includes a first slot and a second slot at opposite ends thereof for inserting therethrough a second end of said first member such that the second end of the first member is inserted into said first slot in order to form the closed loop; and wherein the frangible section that is locked within, the housing may be removed through the second slot.

20. A reusable security seal as claimed in claim 19, wherein a window is provided on the housing between the first and second slots for displaying the identity of the frangible section located within the housing.

21. A reusable security seal as claimed in claim 19, further including cover means for hiding the identity of each of said frangible sections.

22. A reusable security seal as claimed in claim 19, wherein said clasp portion comprises a claw resiliently mounted in said housing, and which selectively engages an internal edge of one of the apertures when tension is applied to a portion of said closed loop proximate said first slot of said housing.

* * * * *